United States Patent

Russmann

(10) Patent No.: US 9,504,607 B2
(45) Date of Patent: Nov. 29, 2016

(54) METHOD AND DEVICE FOR STABILIZING THE CORNEA

(75) Inventor: Christoph Russmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 768 days.

(21) Appl. No.: 13/696,266

(22) PCT Filed: May 5, 2011

(86) PCT No.: PCT/EP2011/002235
§ 371 (c)(1),
(2), (4) Date: Jan. 18, 2013

(87) PCT Pub. No.: WO2011/138031
PCT Pub. Date: Nov. 10, 2011

(65) Prior Publication Data
US 2013/0116757 A1 May 9, 2013

(30) Foreign Application Priority Data

May 7, 2010 (DE) .................. 10 2010 020 194

(51) Int. Cl.
*A61N 5/06* (2006.01)
*A61F 9/008* (2006.01)

(52) U.S. Cl.
CPC ...... *A61F 9/008* (2013.01); *A61F 2009/00842* (2013.01); *A61F 2009/00857* (2013.01); *A61F 2009/00872* (2013.01)

(58) Field of Classification Search
CPC ..................... A61B 2009/00872; A61B 9/008
USPC .................................. 606/2, 4, 5
See application file for complete search history.

(56) References Cited

U.S. PATENT DOCUMENTS

| 5,480,396 A | 1/1996 | Simon et al. |
| 5,749,871 A | 5/1998 | Hood et al. |

(Continued)

FOREIGN PATENT DOCUMENTS

| DE | 41 31 361 | 3/1993 |
| DE | 695 20 274 | 8/2001 |

(Continued)

OTHER PUBLICATIONS

International Search Report based on PCT/EP2011/002235 published on Aug. 26, 2011.

(Continued)

*Primary Examiner* — Aaron Roane
(74) *Attorney, Agent, or Firm* — Frommer Lawrence & Haug LLP

(57) ABSTRACT

A method and device to stabilize the cornea with fewer adverse effects. In particular, a greater stability and shorter treatment time are to be made possible. To this end, the cornea is locally irradiated successively at different sites so that collagen fibers are indirectly or directly crosslinked at the irradiated sites. In this way, the collagen fibers are advantageously crosslinked in a spatially resolved manner. Accordingly, the entire eye need not be irradiated with tissue-damaging UV light, and regions having a weaker structure can be locally stabilized selectively. The sites of the cornea are preferably irradiated so that the collagen fibers are ionized in each instance by photoabsorption of a plurality of photons which each have an energy below an ionizing energy of a given molecule. After a short treatment period, strong covalent bonds are formed directly between the collagen fibers. Crosslinking agents need not be used.

12 Claims, 4 Drawing Sheets

(56) References Cited

U.S. PATENT DOCUMENTS

| | | | |
|---|---|---|---|
| 6,099,521 | A | 8/2000 | Shadduck |
| 6,210,399 | B1 | 4/2001 | Parel et al. |
| 6,783,539 | B1 | 8/2004 | Timberlake et al. |
| 2007/0123845 | A1 | 5/2007 | Lubatschowski |
| 2008/0039769 | A1* | 2/2008 | Peyman .................... 604/20 |
| 2008/0114283 | A1 | 5/2008 | Mattson et al. |
| 2010/0114547 | A1* | 5/2010 | Boyden ............ A61K 9/0019 703/11 |
| 2011/0300504 | A1 | 12/2011 | Kasenbacher |

FOREIGN PATENT DOCUMENTS

| | | |
|---|---|---|
| DE | 101 24 358 | 10/2002 |
| DE | 101 38 984 | 3/2003 |
| DE | 10 2005 056 958 | 6/2007 |
| DE | 10 2008 046 834 | 3/2010 |
| DE | 10 2008 051 644 | 4/2010 |
| DE | 10 2008 053 964 | 5/2010 |
| EP | 0484005 | 5/1992 |
| EP | 1 790 383 | 5/2007 |
| WO | WO 2008/052081 | 5/2008 |

OTHER PUBLICATIONS

International Preliminary Report on Patentability dated Nov. 13, 2012.

Russmann et al., *Two wavelength femtosecond laser induced DNA-protein crosslinking*. Nucleic Acids Research, 1998, Oxford University Press, vol. 26 No. 17, pp. 3967-3970.

Russmann et al., *Crosslinking of progesterone receptor to DNA using tuneable nanosecond, picosecond and femtosecond UV laser pulses*, Nucleic Acids Research, 1997, Oxford University Press, vol. 25, No. 12, pp. 2478-2484.

German Search Report for Application No. 10 2010 020 194.4 dated Oct. 12, 2010.

E. Spörl et al., *Biophysical principles of Collagen Cross-Linking*, 2008, DOI 10.1055/s-2008-1027221, ISSN 0023-2165, 225:131-137.

G. Wollensak et al, *Treatment of Keratoconus by Collagen Cross Linking*, Ophthalmologe 2003, 100:44-49. DOI 10.007/s00347-002-0700-3.

\* cited by examiner

METHOD AND DEVICE FOR STABILIZING THE CORNEA

The present application claims priority from PCT Patent Application No. PCT/EP2011/002235 filed on May 5, 2011, which claims priority from German Patent Application No. DE 10 2010 020 194.4 filed on May 7, 2010, the disclosures of which are incorporated herein by reference in their entirety.

1. FIELD OF THE INVENTION

The invention is directed to an ophthalmic laser device, particularly for stabilizing a cornea, having a laser whose beam can be focused along a treatment beam path in a treatment area and a control unit for controlling the laser, and to a method for stabilizing a cornea of an eye, wherein the cornea is irradiated by laser light in order to crosslink collagen fibers of the cornea. In this regard, the laser is considered hereinafter as part of the treatment beam path. Accordingly, as regards the configuration, calibration or adjustability of the treatment beam path, this can relate to the laser in particular. Insofar as the preceding statements and statements made hereinafter relate to collagen fibers of the cornea, the same also applies to all other constituent parts of the cornea in addition to or alternatively to collagen fibers.

It is noted that citation or identification of any document in this application is not an admission that such document is available as prior art to the present invention.

A stabilization of the cornea is suitable particularly for treatment of keratoconus, a disease in which the cornea becomes increasingly thinner and bulges outward due to internal pressure in the eye. This leads to a moderate to substantial impairment of vision. Protrusion of the cornea due to corneal thinning is called keratectasia.

Although the total collagen content of the cornea in keratoconus does not differ significantly from that of a healthy cornea, the strength is reduced by a factor of approximately 0.7 (Spörl et al., "Biophysical principles of collagen cross-linking", Klin. Monatsbl. Augenheilkd. 2008 February; 225(2):131-7). Further, the amount of hydroxyproline that can be dissolved out of the keratoconic cornea with pepsin is twice that of a healthy cornea. Both imply a massive disruption of corneal crosslinking—possibly in the tertiary and quaternary structures of the collagen fibers.

In the early stages of keratoconus, eyeglasses are usually still sufficient for correction. Even in this stage, however, some patients already have several eyeglasses of different strengths and visual axes which are sometimes worn in combination with contact lenses because visual acuity and axis can sometimes change within days. As keratoconus progresses, defective vision can generally be compensated by dimensionally stable contact lenses and in more extreme cases with special contact lenses known as keratoconus lenses.

When sufficient visual acuity can no longer be achieved even with contact lenses because the cone is very far advanced or because the contact lenses can no longer be adequately fitted, a photo-oxidative crosslinking of the collagen is generally carried out in the prior art by administering riboflavin (vitamin B2) and irradiating the cornea with UV-A light of approximately 370 nm wavelength over a period of about 30 minutes (Wollensak et al., "Treatment of keratoconus by collagen cross-linking", Der Opbthalmologe, 2003 January, 100(1):44-9). Similar methods are described in U.S. Pat. No. 6,783,539 B1 and US 2008/0114283 A1.

Although riboflavin is a nontoxic substance, it is not known whether or not, or to what extent, toxic reaction products are produced through activation by UV-A light. In particular, the long-term stability and long-term toxicity are unclear. Moreover, application of light-induced crosslinking agents (photosensitizers) such as riboflavin is cumbersome and unpleasant for the patient as is the long treatment period. Generally, irradiation of the eye with UV light is problematic because it can lead to tissue damage, particularly also apart from the cornea actually to be treated. The risk of damage increases as the irradiation period increases.

As a last resort, keratoconus can be treated by keratoplasty, i.e., transplantation of corneal tissue. However, keratoplasty is highly invasive and can sometimes lead to severe adverse effects such as rejection of the transplant. Therefore, it is to be avoided if possible.

It is noted that in this disclosure and particularly in the claims and/or paragraphs, terms such as "comprises", "comprised", "comprising" and the like can have the meaning attributed to it in US. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is the object of the invention to provide a device of the type mentioned in the introduction and a method of the type mentioned in the introduction which make it possible to stabilize the cornea with appreciably reduced adverse effects.

For the method according to the invention for stabilizing the cornea, the cornea is locally irradiated successively at different sites (with respect to a wavelength range of the impinging radiation, an impinging radiation power, and the temporal distribution of the impinging radiation) in such a way that collagen fibers are crosslinked at the irradiated sites. If necessary, for irradiation at different (preferably disjoint) sites, the treatment beam path is optically configured in such a way that the laser beam irradiates only a local portion of the cornea at one time and not the entire cornea.

According to the invention, the crosslinking of the collagen fibers can be carried out indirectly or directly. In indirect crosslinking of collagen fibers, these collagen fibers are chemically bonded indirectly by means of an additional molecule (hereinafter referred to as crosslinking agent). The crosslinking agent bonds to a collagen fiber on the one hand and to another collagen fiber on the other hand. Conversely, in direct crosslinking a collagen fiber is chemically bonded directly to another collagen fiber without incorporating another molecule therebetween.

Accordingly, the collagen fibers are advantageously crosslinked in a spatially resolved manner. In this way, regions having a weaker structure can be locally stabilized selectively. In contrast to the prior art, the entire eye need no longer be irradiated by tissue-damaging UV light. This form of the method can be used particularly with exogenic or endogenic molecules which are to be applied to the cornea beforehand—for example, light-induced crosslinking agents such as riboflavin or hyaluronic acid—for indirect crosslinking or exclusively with the collagen fibers of the cornea themselves for direct crosslinking.

According to the invention, it is provided for an ophthalmic laser device that the treatment beam path has a variably adjustable deflection unit for scanning the treatment area and that the control unit is adapted to crosslink collagen fibers of a cornea of an eye arranged in the treatment area by successive irradiation of the cornea at different sites by means of the deflection unit. The treatment area is the area in which a cornea to be treated can be positioned in the treatment position of the patient. The variably adjustable deflection unit allows the treatment beam path to be angled in an adjustable manner for moving the laser beam relative to the treatment area, i.e., relative to the cornea. Accordingly, the control unit can advantageously crosslink the collagen fibers in a spatially resolved and therefore locally selective manner so as to spare the eye and surrounding tissue.

The construction of the control unit for crosslinking collagen fibers by successive irradiation at different sites can be realized, for example, in that the control unit has an operator control by means of which the successive irradiation at the different sites of the cornea can be initiated by an operator for purposes of spatially resolved crosslinking in combination with a software module of the control unit for controlling the deflection unit according to predefined irradiation control data. The irradiation control data advisably include coordinates, including respective radiation power and irradiation time, which are converted by the control unit into control signals for the deflection unit and the laser or a power modulator (intensity modulator). This form of the laser device can be used particularly with light-induced crosslinking agents such as riboflavin or hyaluronic acid to be applied beforehand to the cornea.

The sites of the cornea are preferably irradiated in such a way that the collagen fibers are ionized in each instance by photoabsorption of a plurality of photons which each have an energy below an ionizing energy of a given molecule, whereupon a direct covalent bond is formed between the collagen fibers. In this instance, "direct" means that two collagen fibers undergo a covalent bonding directly, i.e., without a mediating agent. To this end, the treatment beam path is preferably configured or is adjustable in such a way that when irradiating the cornea the laser beam ionizes a collagen fiber (exclusively) through photoabsorption of a plurality of photons which each have an energy below an ionizing energy of a given electron. The indirect covalent bonds are formed subsequently through a chemical reaction of the collagen radicals generated in this way. Owing to their short length, indirect covalent bonds produce a strong connection of the collagen fibers. Their formation is therefore also known as zero-length crosslinking. Thus an appreciably more effective stabilization of the cornea can be brought about compared to crosslinking with crosslinking agents. Therefore, the use of agents of this kind can be entirely dispensed with. Irradiation with photons having an energy below the ionization limit leads to ionization exclusively over at least a (real) intermediate excitation level. This particularly spares the tissue of the cornea and surrounding tissue because the formation of radicals can be selectively minimized in this way. In all of the embodiment forms of the invention, the photoabsorption can be resonant (single photon absorption or multiphoton absorption) or not resonant (multiphoton absorption).

In particularly preferred embodiment forms, the irradiation is carried out in such a way that the ionization and covalent bonding occur in the region of an amino acid of a given collagen fiber. In this way, the stabilization can be carried out within a short time by crosslinking collagen fibers at an irradiation power which is gentle on tissue because the absorption efficiency of photons in the region of amino acids is surprisingly high. According to theoretical prognoses, a treatment period of from one to two minutes compared with 30 minutes in the prior art is sufficient for treatment of a typical keratoconus. In a correspondingly advantageous laser device, the treatment beam path is configured or is adjustable in such a way that when irradiating the cornea the laser beam ionizes a collagen fiber (exclusively) through photoabsorption of a plurality of photons which each have an energy below an ionizing energy of a given electron. In particular, the excitation of the transition $S_0 \rightarrow S_1$ of the corresponding amino acid of the collagen molecule with one or more photons can be carried out in a resonant manner. The multiphoton excitation of the transition $S_0 \rightarrow S_1$ is gentle on tissue by avoiding direct exposure of the tissue to UV.

For brief treatments of this kind, pulsed laser light, in particular with a pulse duration of femtoseconds, picoseconds or nanoseconds, is advisably used for irradiation. In correspondingly advantageous laser devices, the laser is designed for pulsed emission and in particular emits femtosecond pulses, picosecond pulses or nanosecond pulses. The femtosecond pulses are preferably shorter than 500 fs.

The irradiation is advisably carried out in such a way that the amino acid in question is ionized in the region of a π electron system. In particular, the irradiation (with respect to the wavelength range impinging on the cornea) can advantageously be carried out in such a way that there is brought about in the region of the π electron system a π* excitation of the given π electron system and in particular an ionization at the given π electron system. Limiting to excitation and ionization of π electron systems signifies irradiation with a narrow spectral range and, therefore, a high selectivity so that appreciably fewer adverse effects are caused. In correspondingly advantageous embodiment forms, the treatment beam path is configured or is adjustable in such a way that the laser beam on the cornea comprises a wavelength range by which amino acids of the collagen fibers, particularly π electron systems of amino acids, are excited to π* through photoabsorption of at least one photon having an energy below an ionizing energy of a given electron and are ionized (exclusively) through photoabsorption of a plurality of photons each having an energy below an ionizing energy of the given electron.

In particularly preferred embodiments, laser light in a range between 260 nm and 290 nm, particularly between 275 nm and 285 nm, or an integral multiple thereof, particularly a times-one, times-two, times-three or times-four, is used for irradiation. In this way, virtually exclusively π electron bonds of amino acids are excited to π* and, in particular, ionized. In connection with the local selectivity through scanning of the cornea, the treatment can be carried out so as to be extremely sparing on tissue. In correspondingly advantageous devices, the treatment beam path is configured or is adjustable in such a way that the laser beam on the cornea comprises a wavelength range between 260 nm and 290 nm, particularly between 275 nm and 285 nm, or an integral multiple thereof, particularly a times-three or a times-four. Multiphoton absorption occurs with integral multiples of the photoabsorption wavelength, i.e., in the visible or near infrared. Irradiation with visible or infrared light signifies drastically reduced damage to the cornea and surrounding tissue from irradiation. In correspondingly advantageous laser devices, the laser emits ultraviolet light, visible light or infrared radiation and the treatment beam path has a frequency multiplier. Infrared radiation is especially advantageous because it has a high penetration depth so that direct crosslinking between collagen fibers deep within the cornea is also possible.

The excitation and ionization can be achieved with precisely one wavelength range, for example, by the frequency quadruple (fourth harmonic) of a solid state laser (Nd:YAG; Nd:Glas, Ti:Sa, Nd:YLF). For example, the generator (fourth harmonic generator; FHG) can be an arrangement of the birefringent crystals BBO (β-barium borate), KDP (potassium dihydrogen phosphate), KTP (potassium titanyl phosphate) or lithium niobate. Alternatively, irradiation with two disjoint wavelength ranges, which can be referred to as bichromatic excitation, is advantageous. The wavelength range with the shorter wavelengths can then be used to excite from the ground state, while the wavelength range with longer wavelengths excites the excited electron beyond the ionization limit of the molecule. The bichromatic excitation can be achieved, for example, by combining the fourth harmonic and the first or second harmonic of a solid state laser. Simultaneous application of laser pulses or temporal delay ($\Delta T \approx 0 \ldots 10$ ps) of the first or second harmonic through a delay line is advantageous. Use of optical parametric oscillators is possible.

A given site is irradiated in a temporally offset manner with two pulses of disjoint wavelength ranges, wherein the pulse which impinges later in time has longer wavelengths than the earlier pulse, particularly with a temporal pulse spacing between 0 ps and 10 ps, preferably between 0 ps and 2 ps. With the first pulse, the given molecule is raised from the ground state to the first excited singlet state; with the second pulse, the molecule is ionized. In so doing, the careful treatment of tissue is advantageously improved by reducing the more harmful shorter wavelengths and by giving the singlet channel preference over the triplet channel with the advantage of a larger excitation cross section. In a correspondingly advantageous laser device, the laser emits two disjoint wavelength ranges in a pulsed manner and the treatment beam path has a delay line for a longer-wave wavelength range of the two wavelength ranges for generating a temporal offset between the pulses on the cornea, particularly a temporal pulse spacing between 0 ps and 10 ps, preferably between 0 ps and 2 ps.

During irradiation with the second wavelength range, an irradiation power is used that amounts to a factor of between one and two times an irradiation power at the first wavelength. Accordingly, the cornea and surrounding tissue are given the most sparing treatment possible. The center wavelength of the second wavelength range is preferably between 340 nm and 700 nm.

The treatment beam path is configured or is adjustable in such a way (with respect to the wavelength range and radiation power delivered to the cornea) that the cornea is free from photodisruption and ablation, and particularly from laser-induced thermal interaction, during irradiation. Tissue damage is avoided in this way. A radiation power having a purely photochemical effect, i.e., which excludes photodisruption or photoablation, can be delivered to the cornea by the treatment beam path in a switchable or permanent manner, e.g., by means of a beam attenuator. Alternatively, the laser can also be regulated adjustably or permanently to a corresponding radiation power without a beam attenuator. With switchable irradiation powers, for example, by means of different switch settings of an attenuator, power modulator or the laser, the laser device can be configured, for example, for laser-surgical incision by means of photoablation or photodisruption in addition to the photochemical crosslinking of collagen fibers.

The invention also comprises an advantageous method in which a position of an existing cut in the cornea of an eye or another lesion of the cornea is determined in a known manner and the cornea is irradiated in the region of the cut for crosslinking. Cuts from earlier treatments can be closed in this way. For example, a corneal flap cut by means of a femtosecond laser or a lenticule can be "sewed on" to the cornea again, figuratively speaking. To this end, irradiation control data for a crosslinking pass are determined from the acquired coordinates of the cut. These method steps can be carried out by the control unit, for example. A detector coupled with the control unit for measuring the cut is advantageous for this purpose. The detector can be coupled into the treatment beam path, for example, by means of a beamsplitter. During measurement, the laser can be operated at a lower illuminating power (by an attenuator, power modulator or direct control). In particular, the cornea can be imaged confocally on the detector and scanned by the deflection unit for measurement. Finally, the operator can initiate the treatment process with photochemical irradiation power by actuating an operator control of the control unit for crosslinking.

In particular, the invention includes the use of a pulsed femtosecond laser with a beam deflection unit for spatially resolved crosslinking of a cornea, particularly at an irradiation power having an exclusively photochemical effect and at photon energies below an ionizing energy of collagen fibers of the cornea.

The crosslinking according to the invention in the photochemical power range of a laser, with or without crosslinking agents, allows crosslinking of the collagen fibers for therapeutic purposes, for example, for the treatment or prevention of keratoconus, for post-operative treatment of cuts in the cornea to restore pre-operative biomechanical stability. In so doing, areas of the cornea that are especially affected can be crosslinked in a targeted manner (customized crosslinking) based, for example, on topographical data and/or wavefront measurement data. If necessary, the application of crosslinking agents can be carried out by means of eyedroppers or by injection into a corneal pocket; the pocket, among others, can be cut by a femtosecond laser.

BRIEF DESCRIPTION OF THE DRAWINGS

Identical parts are designated by identical reference numerals in all of the drawings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
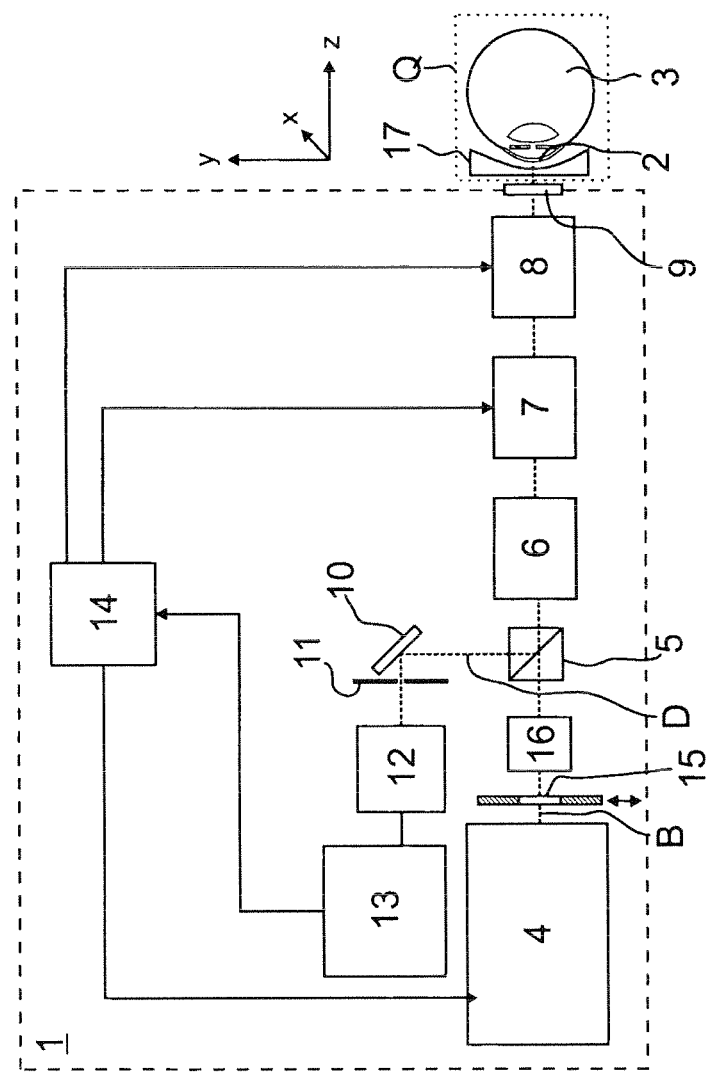
FIG. 1 shows an ophthalmic laser device suitable for surgical cutting at the eye and for monochromatic stabilization of cornea.
Figure 2A:
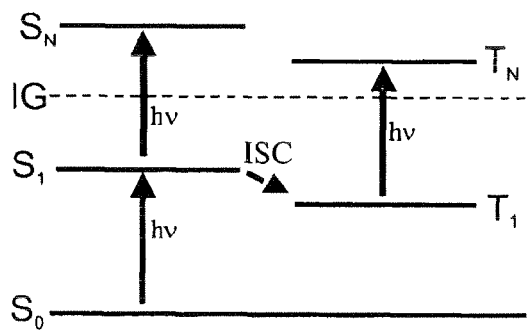
FIG. 2A-2D show Jablonski term diagrams of amino acids.
Figure 2B:
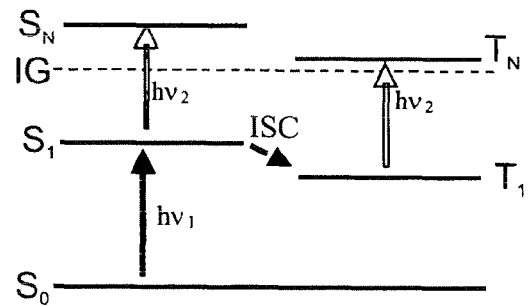
Figure 2C:
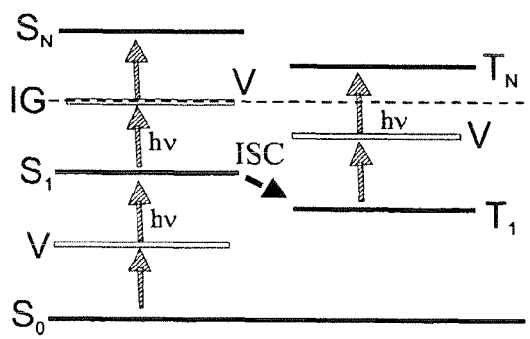
Figure 2D:
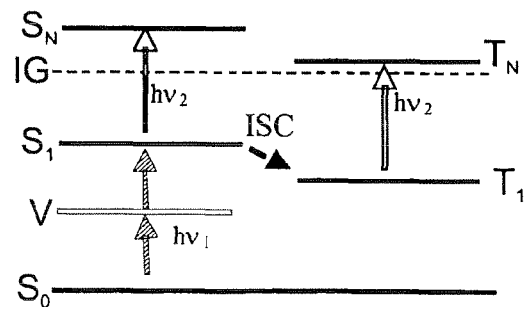

FIG. 1 shows an exemplary ophthalmic laser device 1 which is suitable for clarifying the combined possibility of laser-surgical cutting and stabilizing cornea 2 of an eye 3 in keratoconus. Further, it is configured to identify and locate existing cuts in the cornea 2 with respect to the shape and position thereof in order to crosslink the cornea 2 in the region of such cuts and thus to at least partially close the cuts again. For these purposes, the laser device 1 comprises a laser 4, a polarizing beamsplitter 5, scan optics 6, a deflection unit 7 (also referred to as scanner unit), focusing optics 8, and an exit window 9 which, together with a switchable beam attenuator 15 and a power modulator 16, form an illumination beam path B, and a deflecting mirror 10, a confocal aperture stop 11, and a detector 12 which form a coupled-out detection beam path D. Apart from this, the laser system 1 comprises an amplifier 13 for the detector 12 and a control unit 14. A contact glass 17 with a device for immobilizing the eye 3 is arranged between the laser system 1 and the eye 3; the treatment area Q lies behind this contact glass 17. Other embodiment forms (not illustrated) for realizing the solution according to the invention are possible.

The scanner unit 7 comprises, for example, a quantity of galvanometric mirrors for deflecting the focus volume of the laser radiation in X and Y direction over the cornea 2. The focusing of the laser radiation in Z direction along the optical axis is accomplished, for example, through a movable lens or lens group within the scan optics 6 or focusing optics 8 or, alternatively, through a movable tube lens (not illustrated). The detector 12 is configured, for example, as photomultiplier (PMT) or as avalanche photodiode (APD) because the light intensities to be received are low due to the transparency of the cornea 2. The amplifier 13 is configured as a lock-in amplifier and is connected to both detector 12 and laser 4.

The laser 4 is a pulsed Ti:Sa infrared laser, for example, with a pulse length between 100 fs and 1000 fs. It emits laser radiation at a radiation power suitable for surgical incision. The pulsed IR laser radiation exits from the laser 4 and passes through the polarizing beamsplitter 5, initially without alteration, in the "surgical therapy radiation treatment" switch position. The modulator 16 serves for fine adjustment of the radiation power delivered to the cornea 2. The laser beam is subsequently focused in a target volume in the cornea 2 via the scan optics 3, scanner unit 7 and focusing optics 8. The target volume can be displaced in X, Y and Z direction relative to the cornea 2 by means of the scanner unit 7 and a movable lens or lens group inside the scan optics 6 or focusing optics 8.

In the "illumination radiation power" switch position, the attenuator 15 limits the radiation output so as to rule out alteration of eye tissue through the laser radiation. Dispersion and/or reflection of the IR radiation is then brought about at the interfaces and in the interior of the cornea 2, and the radiation is partially depolarized. Backscattered and/or reflected light also falls in the illumination beam path B, where it retraces its path to the polarizing beamsplitter 5. The portions of radiation with unchanged polarization state fall through the polarizing beamsplitter 5 on the laser 4. This applies particularly to reflections originating from the scan optics 6 or focusing optics 8. Radiation components of this kind which have a changed polarization state due to depolarization in the eye 3 in the cornea 2 are deflected by the polarizing beamsplitter 5 as detection light into the detection beam path D to the detector 12. The detection light falls on the detector 12 via a deflecting mirror 10 through the confocal pinhole diaphragm 11. In an alternative embodiment form (not illustrated), the deflecting mirror 10 can be omitted or can be replaced by other beam guiding units. The confocal diaphragm 11 acts as a discriminator in Z direction so that only backscattered light from a small focus volume is detected in a spatially resolved manner. The control unit 14 can irradiate selected scan points inside the cornea 2 with illumination light by deflecting the illumination light in X and Y direction by means of the deflection unit 7 and changing the focusing in Z direction by means of the focusing optics 8 and can determine the strength of the backscattering at these points by way of the intensity of the associated detection light.

Since the signals recorded at the detector 12 have a very low intensity, the electronic amplifier is adapted for an optimized signal-to-noise ratio. In a particularly advantageous embodiment form, the lock-in amplifier is temporally synchronized with pulse generation or with the repetition rate of the laser 2. Other embodiment forms use, e.g., so-called boxcar techniques or sampling techniques with summing or averaging for noise suppression. The entire amplifier system of the detector signal advantageously has a nonlinear characteristic. A peak detector and/or a sample-and-hold circuit can also be used to achieve improved signals.

In the "photochemical radiation power" switch position of the attenuator 15, an optical output reaching the cornea 2 at most triggers a chemical reaction so that exclusively photochemical interactions with the tissue take place, namely particularly multiphoton absorptions in UV-absorbing π electron bonds of amino acids of the collagen fibers of the cornea 2 and subsequently, by intermediate excitation of an excitation level below the ionizing energy, the ionization of collagen fibers and crosslinking of the resulting radicals.

In other embodiment forms (not illustrated), the laser device can be configured exclusively for stabilizing the cornea so that the laser 4 and/or attenuator 15 are permanently configured for a photochemical radiation power, for example. In this case, the detection beam path D can be omitted. However, other embodiment forms (not illustrated) are also possible in which only the detection of cuts and other lesions of the cornea is combined with stabilization of the cornea and the cutting capability is omitted.

The excitation level of amino acids of the collagen fibers which can be used for crosslinking are shown (not to scale) in FIG. 2 in Jablonski term diagrams. FIG. 2A shows monochromatic excitation through single photon absorption; FIG. 2B shows bichromatic excitation. FIG. 2C shows monochromatic excitation with multiphoton absorption over a virtual intermediate level V. FIG. 2D shows bichromatic excitation with multiphoton absorption from the ground state ($S_0 \rightarrow S_1$) over a virtual intermediate level. The radiated laser light always has a photon energy that is less than the ionizing energy IG.

The wavelength range(s) radiated on the cornea(s) is/are preferably adjusted to fit amino acids such as tryptophan, tyrosine, phenylalanine, proline or hydroxyproline. For the first step, i.e., resonant excitation $S_0 \rightarrow S_1$, a wavelength $\lambda_1$ between 260 and 290 nm (preferably between 275 nm and 185 nm to minimize DNA damage) is necessary. For the second step, $S_1 \rightarrow S_N$, a photon must be radiated with an energy causing ionization of the amino acid proceeding from the excited level. The following condition must be met:

$$E(h \cdot \nu_2) \geq E_{IONIZATION} - h \cdot \nu_1.$$

To meet this condition, it is possible to use UV photons, but wavelengths in the visible region are also sufficient.

In bichromatic crosslinking, UV radiation is preferably used only for the $S_0 \to S_1$ excitation. Accordingly, it is possible to use relatively low UV radiation powers. Further, the singlet path is strongly favored through the subsequent application of a second laser pulse so that there is an extreme reduction in the tissue damage rate.

There are various possibilities for crosslinking through ionization of collagen fibers over real intermediate levels:

1. Resonant Excitation $S_0 \to S_1 \to S_N$ or $S_0 \to S_1 \to T_1 \to T_N$

It is possible to generate crosslinking via the singlet path as well as the triplet path. As a result of the more improbable transitions ISC between singlet systems and triplet systems in terms of quantum mechanics, singlet excitation is more efficient when using femtosecond pulses. After ionization, the transformation takes place—under suitable positioning of the secondary, tertiary and quaternary structures of the collagen fibers—from weak bonds formed with the intermediary of hydrogen bridges to strong covalent bonds.

In addition, the excitation wavelengths radiated on the cornea 2 must satisfy the following conditions:

$$\lambda_1 = \frac{h*c}{\Delta E(S_1 - S_0)}, \quad (1)$$

where
$\lambda_1$=wavelength [nm]
h=Planck constant ($6.62510^{-34}$ Js)
$\Delta E(S_1-S_0)$=energy of the photon for the excitation of $S_0 \to S_1$ [J]
and $$\lambda_2 \leq \frac{h*c}{E_{Ionization} - E(S_1)}, \quad (2)$$

where
$\lambda_2$=wavelength [nm]
$E_{Ionization}-E(S_1)$=energy of the photon for the excitation of $S_1 \to S_N$ [J].

For the monochromatic case, $\lambda_1 = \lambda_2$ and equation (1) applies.

2. Resonant Excitation $S_0 \to S_1 \to S_N$ or $S_0 \to S_1 \to T_1 \to T_N$ (Multiphoton Excitation)

For crosslinking through multiphoton excitation over one or more virtual levels, the excitation wavelengths radiated on the cornea 2 must satisfy the following conditions:

$$\lambda_1 = n*\frac{h*c}{\Delta E(S_1 - S_0)}, \quad (3)$$

where
n=whole number [1, 2, 3 . . . ]
and $$\lambda_2 \leq n*\frac{h*c}{E_{Ionization} - E(S_1)}. \quad (4)$$

For the monochromatic case, $\lambda_1 = \lambda_2$ and equation (3) applies.

By means of infrared femtosecond laser radiation, as is shown by way of example in FIG. 1, multiphoton processes are induced in the molecules of the collagen fibers which finally lead to ionization of the molecule over at least one real intermediate excitation level. The radiation power must be high enough to trigger multiphoton absorptions, but no photodisruption (optical breakdown) or ablation may be induced.

Figure 3:
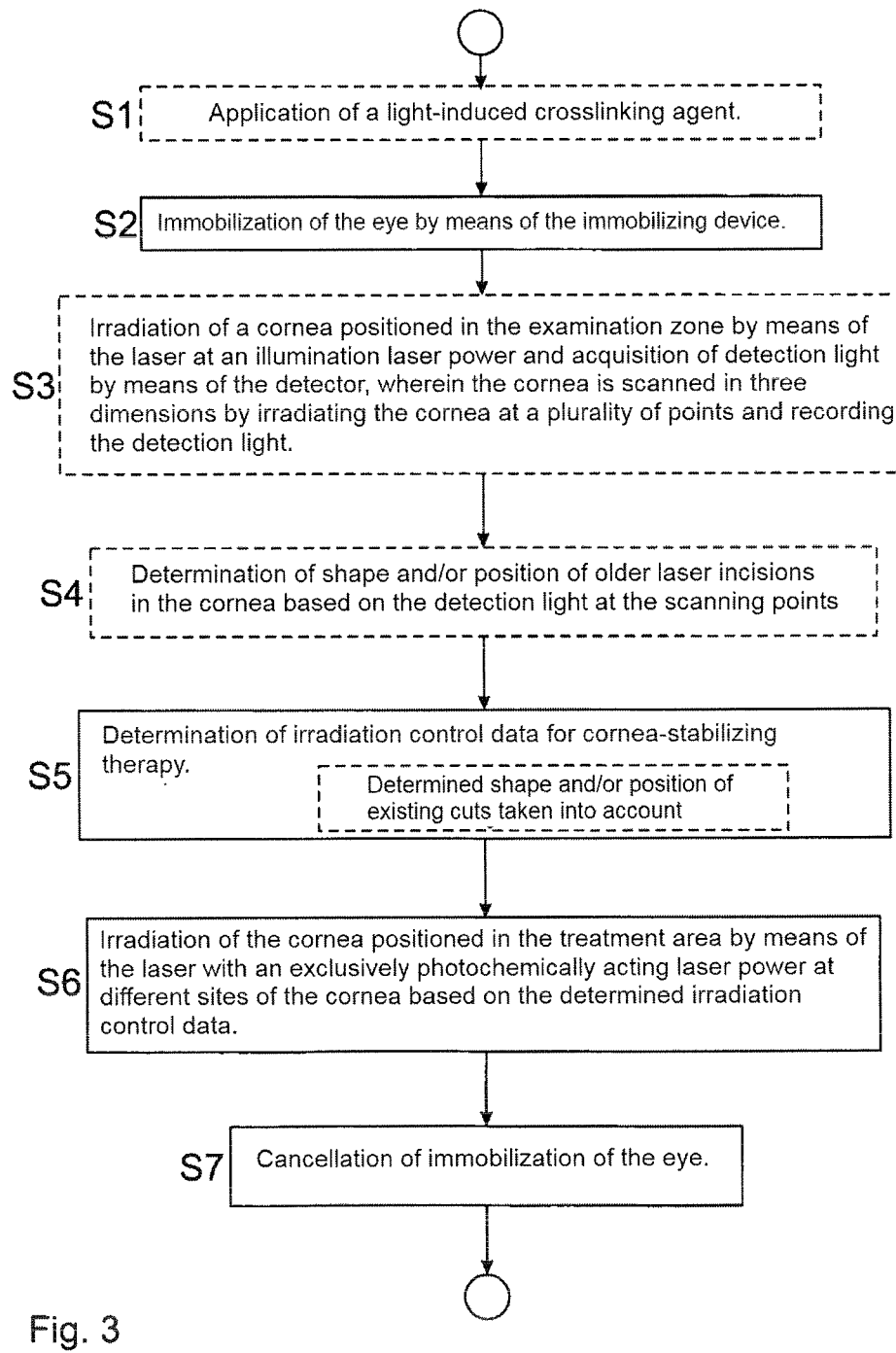
FIG. 3 shows the sequence of a method for spatially resolved crosslinking.

The control unit 14 carries out, for example, the operating method shown in FIG. 3, wherein step S1, framed in dashed lines, is typically carried out manually by the operator but only when a crosslinking agent is to be used. In so doing, the laser 4 is used for illumination during the detection phase as well as for the crosslinking of collagen fibers of the cornea 2 during the immediately following treatment phase. In case treatment is to be performed exclusively, steps S2 and S3, framed in dashed lines, and sub-step S5, framed in dashed lines, are not executed.

First, the patient's eye 3 is immobilized, for example, suctioned by means of negative pressure at a contact glass device (step S2). The head of the patient may be immobilized in addition. The gaze of the patient can be kept as constant as possible by means of a suitable target.

The illumination light is guided over the cornea 2 along an adjustable, continuous, three-dimensional scanning curve or scanning pattern at illumination laser power with a variable pulse frequency and detection light is received (step S3). In so doing, the pulse frequency is adjusted as a function of the speed of the scanning movement in such a way that a pulse frequency during a slower scanning movement is lower than during a faster scanning movement. The backscattered detection light is associated segment by segment or point by point with individual points of the scanning curve. Successive scanning points in all spatial coordinates are distinguished through the continuity of the scanning curve. In an advantageous manner, respective darkfield values which are determined in a separate calibration pass are subtracted from the detected signal values.

Existing cuts are identified from the intensities associated with the scanning points and the shape and position thereof are reconstructed (step S4). To this end, for example, scanning points whose intensity exceeds an intensity threshold which is predefined or predefinable by the operator are determined as reference points of the cut. An assumed model of the cut, or one that is known from a previous treatment, is fitted to the three-dimensional coordinates of the determined reference points of the old cut by a best-fit calculation in order to make all of the coordinates of the old cut available as a basis for the crosslinking of the cut.

Subsequently, irradiation control data are determined (step S5). The irradiation control data include, for example, control signals for the axes of the scanner unit 7 or for the internal Z focusing and for the laser beam source and power modulator 16. The irradiation control data are determined, for example, from defaults which are queried from a database via a software interface or by the operator via a graphical user interface. In particular, topographical data, wavefront data, data of an ultrasound measurement or OCT measurements of the cornea 2 to be treated, the spatial information concerning a keratoconus, existing cuts and/or other areas to be crosslinked are taken into account when determining the irradiation control data. Insofar as existing cuts are identified, the data obtained in so doing can likewise be used in determining the irradiation control data in order to determine the sites at which crosslinking is to be carried out. For example, the sites to be irradiated along the cut can be calculated.

Immediately afterwards, the irradiation is carried out (step S6) based on the irradiation control data at a laser power having exclusively a photochemical effect. In so doing, the control unit 14 adjusts the beam attenuator 15 to the switch position for radiation power having at most a photochemical effect and moves the deflection units 7 and 8 in accordance with the irradiation data. At every site to be irradiated, it controls the power modulator 16 according to the irradiation control data so as to introduce the determined radiation energy into the cornea 2. On the basis of the infrared radiation of the laser 4, monochromatic crosslinking, for example, is carried out by multiphoton absorption corresponding to FIG. 2C. Finally, the immobilization of the eye 3 is canceled (step S7).

Through use of adapted scanning curves (scanning patterns), for example, in the form of spatially extended Lissajous figures, i.e., two overlapped, particularly harmonic oscillations such as spatially offset figure-eights, it is possible to measure existing cuts in a short time, for example, within at most 30 seconds, which reduces movement inaccuracies on the one hand and leads to a higher acceptance on the part of the patient on the other hand. Other exemplary scanning shapes (not illustrated) may include: two crossed rectangles in space; two cylinder surfaces; a cylindrical body with cross section in the shape of an eight or a four; a plurality of scans along one-dimensional lines. It is also possible to raster scan the volume of a cylinder or cube. The volumes or surfaces can be scanned continuously or only partially, i.e., with gaps between the individual scanning points. Accordingly, greater distances may occur between individual lines.

It is possible to make allowances for particulars of the patient's eye 3, for example, the sites to be crosslinked or the required crosslinking efficiency, etc., by adapting the scanning curves, varying the distances between sites (spots), varying the pulse energy and varying the pulse frequency, among others.

Figure 4:
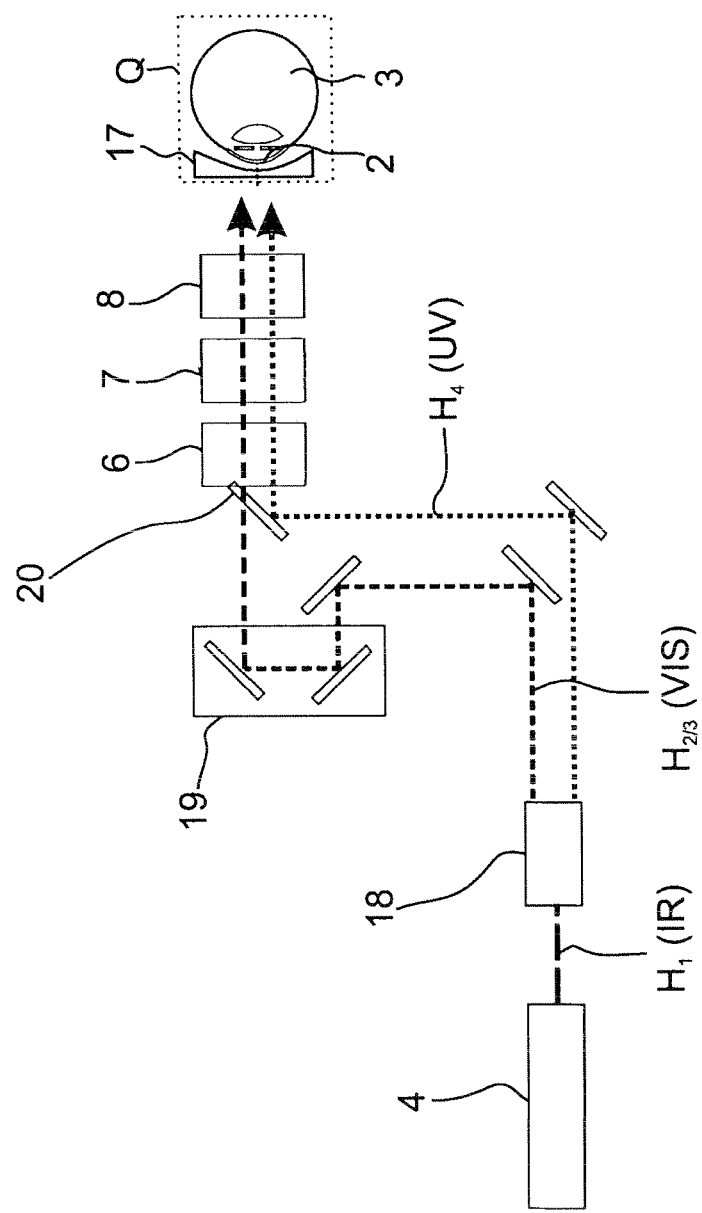
FIG. 4 shows an ophthalmic laser device for temporally offset bichromatic stabilization of cornea.

Another laser device 1 for bichromatic crosslinking is shown schematically in FIG. 4. In a frequency multiplier 18, for example, a quadruplet (FHG), the infrared beam (first harmonic $H_1$) of the pulsed femtosecond solid state laser 1 is split spatially and spectrally into two beams: into the second or third harmonic $H_{2/3}$ in a green or blue wavelength region on one hand and into the fourth harmonic $H_4$ in the ultraviolet wavelength region on the other hand. Beam $H_{2/3}$ with the longer-wave green/blue wavelength range is guided along a delay line 19 and recombined with the other beam $H_4$ at a beam recombiner 20. Both beams are then guided together in the same focus volume in the cornea 2. The delay line 18 can be adjusted to different delays between 0 ps and 10 ps, for example, by mirrors which are displaceable along the optical axis. The green or blue pulses reach the cornea 2 later than the ultraviolet pulse by this amount of delay. Instead of a delay line 19, a coaxial-dispersive element can be used.

In all of the embodiment forms, a device for tracking movements of the eye (eye tracker) can be used in order to carry out corrections in the irradiation control data.

Nanosecond pulses or picosecond pulses, for example, can be used instead of light pulses of femtosecond lasers. Insofar as crosslinking agents are used, other light sources and, in particular, continuous wave irradiation (cw) are also possible during the scanning of different sites of the cornea 2.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMERALS 1 laser device
2 cornea
3 eye
4 laser
5 polarizing beamsplitter
6 scan optics
7 deflection unit
8 focusing optics
9 exit window
10 deflecting mirror
11 aperture stop
12 detector
13 amplifier
14 control unit
15 beam attenuator
16 power modulator
17 contact element
18 frequency multiplier
19 delay line
20 beam recombiner
B treatment beam path
D detection beam path
Q treatment area
S singlet state
T triplet state
IG ionizing energy
V virtual intermediate level
ISC intersystem transition
X, Y, Z coordinates
$H_1$ first harmonic
$H_{2/3}$ second/third harmonic
$H_4$ fourth harmonic

The invention claimed is:

1. A method for stabilizing a cornea of an eye, comprising:
irradiating the cornea by laser light in order to crosslink collagen fibers of the cornea;
wherein the cornea is locally irradiated successively at different sites in such a way that the collagen fibers are crosslinked at the irradiated sites, and
wherein the collagen fibers are ionized in each instance through photoabsorption of a plurality of photons each having an energy below the ionizing energy of a respective molecule, whereupon a direct covalent bond is formed between the collagen fibers.

2. The method according to claim 1;
wherein the irradiation is carried out in such a way that the covalent bonding occur in the region of an amino acid of a respective collagen fiber.

3. The method according to claim 2;
wherein the irradiation is carried out in such a way that the respective amino acid is ionized in the region of a π electron system.

4. The method according to claim 1;
wherein laser light in a range between 260 nm and 290 nm, or an integral multiple thereof, is used for irradiation.

5. The method according to claim 1;
wherein pulsed laser light is used for irradiation.

6. The method according to claim 1;
wherein the cornea is free from light-induced crosslinking agents during irradiation.

7. The method according to claim 1;
wherein a position of an existing cut in the cornea of an eye, or another lesion of the cornea, is determined, and the cornea is irradiated in the region of the cut for crosslinking.

8. The method according to claim 1;
wherein the sites are irradiated in such a way that the collagen fibers resonantly absorb the photons.

9. The method according to claim 1;
wherein the sites are irradiated in such a way that the collagen fibers resonantly absorb a plurality of photons in the ground state.

10. A method for stabilizing a cornea of an eye, comprising:
irradiating the cornea by laser light in order to crosslink collagen fibers of the cornea;
wherein the cornea is locally irradiated successively at different sites in such a way that the collagen fibers are crosslinked at the irradiated sites,
wherein a given site is irradiated in a temporally offset manner with two pulses of disjoint wavelength ranges, where the pulse which impinges later in time has a longer center wavelength than the earlier pulse.

11. The method according to claim 10,
wherein, during irradiation with the second wavelength, an irradiation power is used that amounts to a factor between one and two times an irradiation power at the first wavelength.

12. A method for spatially resolved crosslinking of a cornea, comprising:
utilizing a pulsed femtosecond laser with a beam deflection unit to crosslink the cornea by employing an exclusively photochemically acting irradiation power and photon energies below an ionizing energy of collagen fibers of the cornea; and
forming a direct covalent bond between the collagen fibers.

* * * * *